United States Patent [19]

Polaschegg

[11] Patent Number: 5,085,656
[45] Date of Patent: Feb. 4, 1992

[54] IMPLANTABLE DEVICE FOR THE DOSED ADMINISTRATION OF MEDICAMENTS TO THE HUMAN BODY

[75] Inventor: Hans-Dietrich Polaschegg, Oberursel, Fed. Rep. of Germany

[73] Assignee: Annemarie Schlögl GmbH & Co. KG, Pottenstein, Austria

[21] Appl. No.: 521,128

[22] Filed: May 9, 1990

[30] Foreign Application Priority Data

May 20, 1989 [DE] Fed. Rep. of Germany ....... 3915251

[51] Int. Cl.⁵ .............................................. A61M 5/00
[52] U.S. Cl. .................................. 604/891.1; 604/132
[58] Field of Search ................. 119/890.1, 891.1, 131, 119/132, 141

[56] References Cited

U.S. PATENT DOCUMENTS

| 3,951,147 | 4/1976 | Tucker et al. | 604/891.1 |
| 4,140,122 | 2/1979 | Kühl et al. | 128/260 |
| 4,581,018 | 4/1986 | Jassawalla | 604/891.1 |
| 4,619,652 | 10/1986 | Eckenhoff et al. | 604/891.1 |
| 4,668,231 | 5/1987 | de Vries et al. | 604/891.1 |
| 4,718,430 | 1/1988 | Holzer | 604/890.1 |
| 4,772,263 | 9/1988 | Dorman et al. | 604/891.1 |
| 4,777,953 | 10/1988 | Ash et al. | 128/635 |
| 4,820,273 | 4/1989 | Reinicke | 604/891.1 |
| 4,854,322 | 8/1989 | Ash et al. | 128/635 |
| 4,886,514 | 12/1989 | Maget | 604/891.1 |
| 4,898,582 | 2/1990 | Faste | 604/141 |
| 4,969,873 | 11/1990 | Steinbach et al. | 604/891.1 |

Primary Examiner—Paul J. Hirsch

[57] ABSTRACT

An implantable device for the dosed administration of medicaments to the human body includes a first chamber for storing a medicament and having a refill opening sealed by a pierceable septum and an outlet opening communicating with an outlet catheter, a second chamber separated from the first chamber by a flexible diaphragm which serves to apply pressure to the medicament, and a hollow fiber capillary filter disposed at the outlet opening of the first chamber to act as a filter.

20 Claims, 1 Drawing Sheet

IMPLANTABLE DEVICE FOR THE DOSED ADMINISTRATION OF MEDICAMENTS TO THE HUMAN BODY

1. FIELD OF THE INVENTION

The present invention relates to an implantable device for the dosed administration of medicaments to the human body.

2. DESCRIPTION OF THE PRIOR ART

An implantable device of this type is known from Austrian patent specification 1631/88 and corresponding, commonly assigned U.S. patent application Ser. No. 07/370,328 filed June 22, 1989, now U.S. Pat. No. 4,969,873 in the names of Steinback and Schloegl. The respective disclosures of each of Austrian patent specification 1631/88 and U.S. patent application Ser. No. 07/370,328 now U.S. Pat. No. 4,969,873 are incorporated herein by reference. This device comprises a housing which has arranged therein a first storage chamber for the element to be dispensed. This chamber can be refilled via a pierceable septum and is connected via an outlet opening and an outlet reducing means in the form of a hose winding to an annular chamber which leads to an outlet catheter. The medicament provided in the first chamber is supplied to the outlet catheter by the application of pressure, for which purpose a second chamber is provided which is filled with a propellant expanding at body temperature, and is separated by a diaphragm from the first chamber.

Such implantable devices or pumps are used for the continuous medication of patients who, otherwise, could only be treated by injecting medicaments several times a day. Especially when painkillers are administered, great demands must be made on the safety of such pumps because an overdose of such painkillers has often a lethal effect, and any misuse must moreover be excluded.

The problem arising in the device described at the outset and in other, similarly constructed pumps (German patent application 2 626 348 and corresponding U.S. Pat. No. 4,140,122 issued Feb. 20, 1979 consists in that when germs are introduced, the same may propagate rapidly and that particles which are caused by the piercing of the septum may clog either the outlet reducing means or the outlet catheter.

To avoid this drawback, it has been suggested for some known pumps that filters should be installed either between an inlet chamber or the reservoir or between the reservoir and the pump mechanism, or that the line which leads from the reservoir to the pump mechanism should be provided with a number of holes at the reservoir side. In the latter case, however, these holes or pores are so great that they cannot keep back bacteria. Moreover, said pores in said arrangement are only intended to prevent blockage of the suction opening when the supply vessel collapses. Flat diaphragm filters which are fixedly clamped in a holding device are used for the above-mentioned pumps. This construction, however, needs a lot of space which, as far as an implantable pump is concerned, should of course be kept as small as possible. Moreover, it is diffult to seal the diaphragm and to check the tightness thereof. Therefore, the above-mentioned problem has so far not been solved in a satisfactory way.

Furthermore, as far as the technological background is concerned, reference is made to German patent application 3 806 008 and corresponding U.S. Pat. Nos. 4,777,953 and 4,854,322 issued Oct. 18, 1988 and Aug. 8, 1989, respectively, which describe a capillary filtration and collection device for a very special application, and to German patent application 3 518 841 from which the provision of a septum is known per se.

SUMMARY OF THE INVENTION

It is therefore the object of the present invention to provide an implantable device which is used for the dosed administration of medicaments to the human body and with which it is possible to avoid the risk of clogging of the outlet reducing means or the outlet catheter.

This object is attained through an implantable device which is used for the dosed administration of medicaments to the human body and which comprises a first chamber for storing a medicament, said chamber being provided with a refill opening sealed by means of a pierceable septum and being connected via an outlet opening and optionally via an outlet reducing means to an outlet catheter, and a second chamber which is separated by a flexible diaphragm from the first chamber and serves to apply pressure via the diaphragm to the medicament provided in the first chamber, said device being characterized in that a hollow fiber capillary which is arranged at the outlet end of the first chamber is provided as a filter.

Owing to the provision of a hollow-fiber capillary filter which at one end is e.g. connected to the outlet reducing means, particles which have penetrated into the first chamber are definitely prevented from entering into the outlet reducing means and the outlet catheter. As a consequence, said two members cannot become clogged. This increases the reliability of the device of the invention to a considerable extent.

According to the present invention the implantable device has also the advantage that the described sealing can be attained in a simple way without additional sealing problems resulting therefrom. Moreover, the hollow fiber capillary needs little space and can be arranged in one or a plurality of windings in the first chamber forming the supply container. This avoids the risk of clogging caused by particles which under the action of gravitation preferably deposit at some place in the first chamber.

The subclaims relate to advantageous developments of the invention.

If the implantable device comprises a passage opening through which the first chamber is connected to the outlet reducing means, the hollow fiber capillary connected previously to the outlet reducing means is guided through the passage opening into the first chamber in which it is then arranged with one or a plurality of windings.

In an especially preferred embodiment the hollow fiber capillary is inserted inside the first chamber into a groove which is arranged above the diaphragm. This prevents the closing of the hollow fiber capillary by the diaphragm when the medicament supply decreases, which can additionally be supported by the construction of the diaphragm and the inner space of the first chamber.

The filtration surface of the microporous hollow fiber capillary can be considerably increased by forming one or a plurality of windings, so that clogging of the hollow fiber capillary itself due to the particles located in the first chamber can definitely be prevented.

Preferably, the hollow fiber capillary has an inner diameter of about 200 μm and an outer diameter of about 280 μm. When the outlet reducing means is formed as a reducing capillary, one end of this reducing capillary can be slid over the corresponding connection end of the hollow fiber capillary, or, inversely, the corresponding end of the hollow fiber capillary is slid some millimeters over the end of the reducing capillary, whereupon the two capillary ends are connected with the aid of an adhesive, preferably polyurethane.

Either a conventional dialyzer diaphragm or, however, a diaphragm which is used for plasma filtration or plasma fractionation and has a higher exclusion capacity may preferably be employed as a hollow-fiber capillary filter. Such a diaphragm is normally closed at one of its front ends.

Description of the Drawings

Other details, features and advantages of the invention will become apparent from the following description of an embodiment with reference to the drawing, wherein

FIG. 1 shows an implantable device or pump 1 of the invention which is used for the dosed administration of medicaments to the human body. The device 1 comprises a housing which is composed of two housing members 1' and 2 and whose inner space is divided by a flexible diaphragm 3 into a first chamber 4 and a second chamber 5. The first chamber 4 serves to accommodate the medicament to be administered, whilst the second chamber 5 serves to apply pressure via the diaphragm 3 to the medicament provided in the first chamber 4. For this purpose the second chamber 5 may e.g. be filled with a propellant which isobarically expands on account of the body heat. As a result of the expansion of the propellant, pressure is applied to the diaphragm 3, so that the volume of the first chamber 4 decreases and the medicament is thereby displaced from the chamber 4. The medicament is here dispensed into the patient's body via an outlet opening 6 communicating with the chamber 4, an outlet reducing means 7 communicating with the outlet opening 6, and an outlet catheter 8. Before the medicament reaches the outlet catheter 8, it is introduced into a chamber 9 which is annularly disposed in the member 1' of the housing. In the embodiment shown, said chamber 9 is closed on its upper side by a ring 10 which can be pierced by a hypodermic needle and which is automatically sealed again after the hypodermic needle has been withdrawn. The ring 10 is held in position with the aid of an annular fastening means 11.

Furthermore, the first chamber 4 comprises a refill opening 12' which is closed by a second septum 12 retained by a fastening member 13. Said septum 12 can also be pierced by a hypodermic needle for filling medicaments into the first chamber 4 again.

Figure 1:
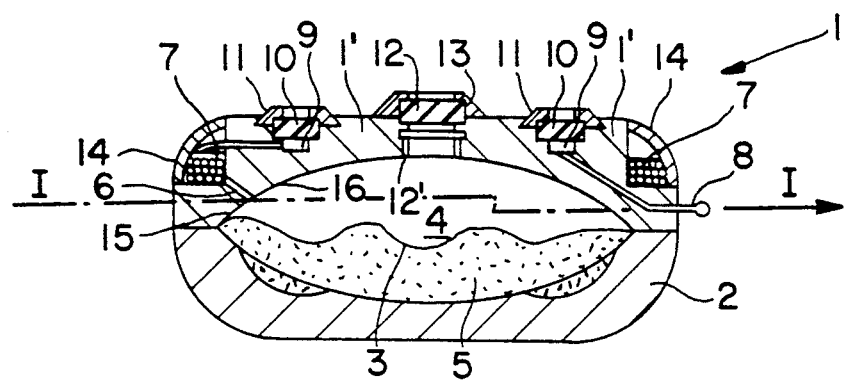
FIG. 1 is a vertical section through a device of the invention and FIG. 2 a section along line I—I of FIG. 1.

In the embodiment shown in FIG. 1, the implantable device 1 is constructed as a rotational body, the refill opening 12' being arranged centrically and the annular chamber 9 being disposed concentrically around the refill opening 12'.

Figure 2:
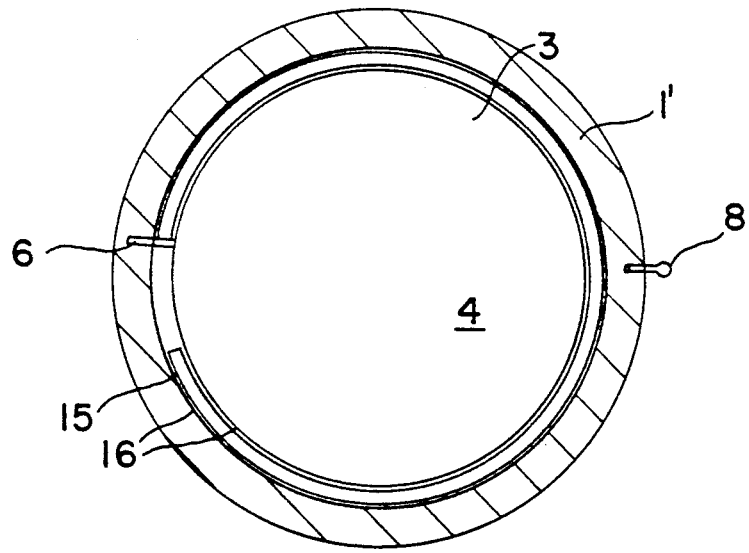

In the embodiment shown in FIGS. 1 and 2, the outlet reducing means 7 is constructed as a hose winding or as a reducing capillary which is wound in a recess of the member 1' of the housing several times. The recess is sealed by a cover 14 in such a way that a smooth outer contour of the implantable device 1 is attained.

The chamber 9 and thus the sealing ring 10 are concentrially disposed around the refill opening 12'.

In the implanted state the device or pump 1 continuously dispenses the medicament provided in the first chamber 4, into the patient's body via the outlet catheter 8. If for reasons of health a greater amount of this medicament or another additional medicament is to be administered to the patient's body, the ring 10 is pierced by means of a syringe whose point of puncture is determined by a template (not shown in greater detail in the figures) which is placed on the body, and the medicament to be dispensed is injected into the chamber 9 from which it is directly administered to the body through the outlet catheter 8. The flow resistance in the outlet reducing means 7 is here so great that the medicament cannot press back into the first chamber 4 of the implantable device.

As described at the outset, particles may however accumulate when the septum 12 or the septum 10 is pierced, and these particles may clog either the outlet reducing means 7 or the outlet catheter 8 or both members, which might reduce the operativeness of such a device or even disable the same. For this reason the device 1 of the invention comprises an additional filter in the form of a hollow fiber capillary 15 which is connected at one end to the inlet end of the outlet reducing means and guided through the outlet opening 6 into the interior of the first chamber 4 in the embodiment shown in FIG. 1. In the chamber 4 a groove 16 is arranged above the diaphragm 3, and the section of the hollow fiber capillary 15 which is introduced into the first chamber 4 can be inserted thereinto.

As illustrated in FIG. 1, the groove 16 is arranged above the diaphragm 3, so that the section of the hollow fiber capillary which is provided in the chamber 4 is not closed when the medicament supply decreases.

As illustrated in FIG. 2, the section of the hollow fiber capillary 15 which has been introduced into the chamber 4 is wound in this embodiment. In principle, it is also possible to form a plurality of such windings for increasing the filter surface.

As has been described, the device 1 which is illustrated by way of example in FIGS. 1 and 2 is provided with an outlet reducing means to which one end of the hollow fiber capillary 15 is connected. If such an outlet reducing means is not provided, which is the case with some pumps, the hollow fiber capillary will then of course be connected to a corresponding suitable member, which, however, does not at all alter the above-described filtering effect for preventing clogging in line sections inside the device or of the outlet catheter 8. Hence, it would in principle be possible that at the outlet side an end of the hollow fiber capillary 15 is directly connected to the outlet opening or e.g. directly to the annular chamber 9 if for some reason or other an outlet reducing means 7 is not to be provided, as stated above.

In any case this has the advantage that clogging is definitely prevented by the provision of the hollow-fiber capillary filter 15 which can be arranged in a reliable and space-saving way.

I claim:

1. An implantable device (1) for the dosed administration of medicaments to the human body, comprising
a first chamber (4) for storing a medicament, said chamber being provided with a refill opening (12') sealed by means of a pierceable septum (12), and connected via an outlet opening (6) to an outlet catheter (8); and a second chamber (5)

which is separated by a flexible diaphragm (3) from said first chamber (4) and serves to apply pressure via said diaphragm (3) to said medicament provided in said first chamber (4), characterized in that a porous hollow fiber capillary (15) disposed at the outlet opening of said first chamber (4) is provided as a filter.

2. An implantable device (1) according to claim 1, characterized in that an outlet reducing means (7) connecting said outlet opening (6) to said outlet catheter (8) is provided, one end of said outlet reducing means (7) being disposed adjacent said outlet opening (6) and connected to an end of said porous hollow-fiber capillary (15).

3. An implantable device (1) according to claim 1, characterized in that said hollow fiber capillary (15) is guided through the outlet opening (6) into said first chamber (4).

4. An implantable device (1) according to claim 1, characterized in that said hollow fiber capillary (15) is inserted inside said first chamber (4) into a groove (16) which is disposed above said diaphragm (3).

5. An implantable device (1) according to claim 1, characterized in that said hollow fiber capillary (15) is disposed in at least one winding in said first chamber (4).

6. An implantable device (1) according to claim 1, characterized in that said hollow fiber capillary (15) has an inner diameter of about 200 μm.

7. An implantable device (1) according to claim 6, characterized in that said hollow fiber capillary (15) has an outer diameter of about 280 μm.

8. An implantable device (1) according to claim 1, characterized in that a conventional dialyzer diaphragm of polysulfone is used as said hollow fiber capillary (15).

9. An implantable device (1) according to claim 1, characterized in that a diaphragm which is usable for plasma filtration or plasma fractionation and has a higher exclusion capacity is employed as said hollow fiber capillary (15).

10. An implantable device (1) according to claim 1, characterized in that said hollow fiber capillary (15) is closed on one side.

11. An implantable device (1) according to claim 2, characterized in that said hollow fiber capillary (15) is adhered to an end of said outlet reducing means (7).

12. An implantable device (1) according to claim 11, characterized in that polyurethane is used as an adhesive for adhering said hollow fiber capillary to said end of said outlet reducing means (7).

13. An implantable device (1) for the dosed administration of medicaments to the human body, comprising a first chamber (4) for storing a medicament, said chamber being provided with a refill opening (12') sealed by means of a pierceable septum (12), and connected via an outlet opening (6) to an outlet catheter (8); and a second chamber (5)

which is separated by a flexible diaphragm (3) from said first chamber (4) and serves to apply pressure via said diaphragm (3) to said medicament provided in said first chamber (4), characterized in that porous hollow fiber capillary (15) guided through the outlet opening (6) into said first chamber (4) is provided as a filter.

14. An implantable device (1) according to claim 13, characterized in that an outlet reducing means (7) connecting said outlet opening (6) to said outlet catheter (8) is provided, one end of said outlet reducing means (7) being disposed adjacent said outlet opening (6) and connected to an end of said porous hollow fiber capillary (15).

15. An implantable device (1) according to claim 13, characterized in that said hollow fiber capillary (15) is inserted inside said first chamber (4) into a groove (16) which is disposed above said diaphragm (3).

16. An implantable device (1) according to claim 13, characterized in that said hollow fiber capillary (15) is closed on one side.

17. An implantable device (1) for the dosed administration of medicaments to the human body, comprising a first chamber (4) for storing a medicament, said chamber being provided with a refill opening (12') sealed by means of a pierceable septum (12), and connected via an outlet opening (6) to an outlet catheter (8); and a second chamber (5)

which is separated by a flexible diaphragm (3) from said first chamber (4) and serves to apply pressure via said diaphragm (3) to said medicament provided in said first chamber (4), characterized in that a porous hollow fiber capillary (15) disposed at the outlet opening of said first chamber (4) is provided as a filter, wherein said hollow fiber capillary (15) is inserted inside said first chamber (4) into a groove (16) which is disposed above said diaphragm (3).

18. An implantable device (1) according to claim 17, characterized in that outlet reducing means (7) connecting said outlet opening (6) to said outlet catheter (8) is provided, one end of said outlet reducing means (7) being disposed adjacent said outlet opening (6) and connected to an end of said porous hollow fiber capillary (15).

19. An implantable device (1) according to claim 17, characterized in that said hollow fiber capillary (15) is guided through the outlet opening (6) into said first chamber (4).

20. An implantable device (1) according to claim 1, characterized in that said hollow fiber capillary (15) is closed on one side.

* * * * *